United States Patent [19]
Foster

[11] Patent Number: 5,920,038
[45] Date of Patent: Jul. 6, 1999

[54] STETHOSCOPE DEVICE ASSEMBLY

[76] Inventor: Kevin L. Foster, 376 S. Oakland Ave., Pasadena, Calif. 91101

[21] Appl. No.: 08/979,164

[22] Filed: Nov. 26, 1997

[51] Int. Cl.$^6$ .......................................................... A61B 7/02
[52] U.S. Cl. ............................................ 181/131; 181/137
[58] Field of Search ................................... 181/131, 137; 381/67; D24/134

[56] References Cited

U.S. PATENT DOCUMENTS

| | | | |
|---|---|---|---|
| D. 230,212 | 1/1974 | Hart | D24/134 |
| D. 284,790 | 7/1986 | Moore | D24/134 |
| D. 349,959 | 8/1994 | Troiani | D24/134 |
| 4,461,368 | 7/1984 | Plourde | 181/131 |
| 4,475,619 | 10/1984 | Packard | 181/137 |
| 4,569,413 | 2/1986 | Allen | 181/131 |
| 4,867,268 | 9/1989 | Ulert | 181/137 |

*Primary Examiner*—Khanh Dang
*Attorney, Agent, or Firm*—Frederick Gotha

[57] ABSTRACT

A stethoscope device assembly which is adapted to monitor a surface sound on a body surface of a mammalian body and includes an earpiece assembly which is acoustically coupled to a sound receiver assembly. A sound transmission member is coupled to and extends between the earpiece assembly and the sound receiver assembly. An arm which includes at least a portion of the sound transmission member and also a superelastic member is coupled to and extends between the earpiece assembly and the sound receiver assembly. The superelastic member has a resting shape, such as a helical shape, which is adjustable under an applied force to a strained shape, and also has an elastic memory to the resting shape after being adjusted to the strained shape. The resting shape of the superelastic member minimizes the arc about which the sound receiver assembly may swing when the stethoscope is worn by a user such that the earpiece assembly is engaged to the user's head or neck and the arm extends vertically downward therefrom along the user's chest. A transducer diaphragm is removably engageable with a housing of the sound receiving assembly and also bears visible indicia which is adapted to pacify an apprehensive patient. A plurality of the transducer diaphragms is provided, each having a different indicia than the other transducer diaphragms such that a patient or healthcare provider/user of the stethoscope may chose one of the transducer diaphragms based upon its respective indicia.

13 Claims, 3 Drawing Sheets

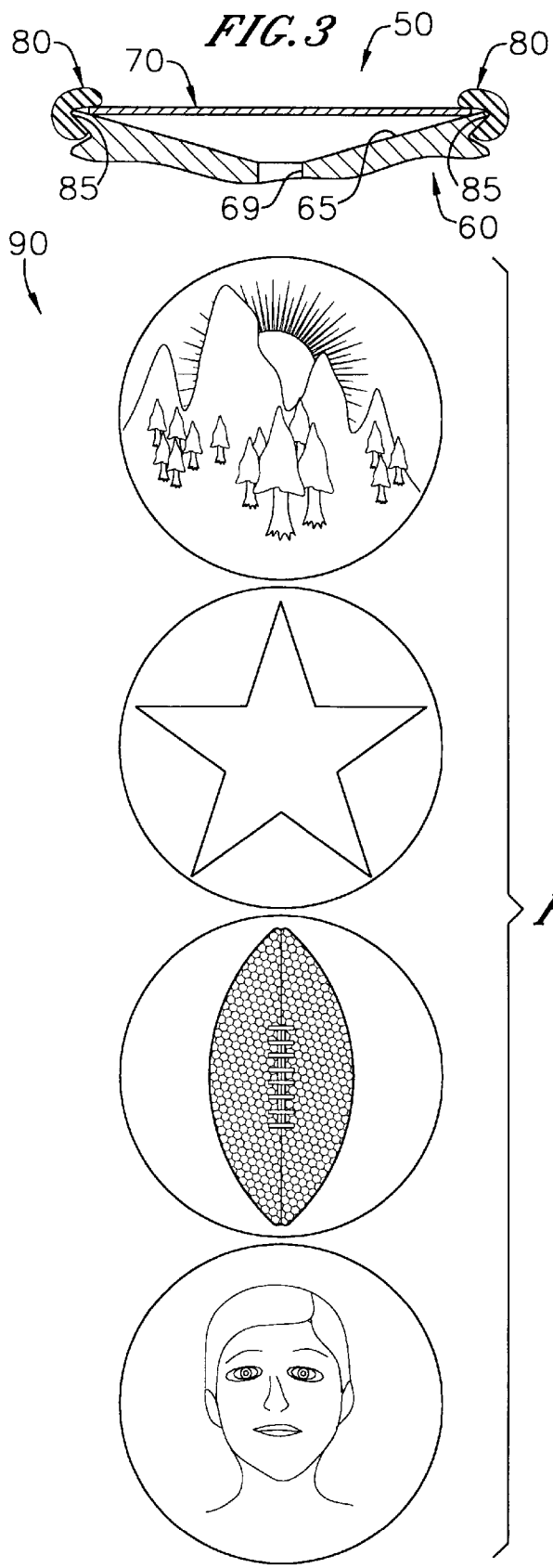

STETHOSCOPE DEVICE ASSEMBLY

TECHNICAL FIELD

The present invention is a stethoscope device assembly for monitoring surface sounds on a body surface of a mammalian body. More particularly, it is a stethoscope device assembly that provides a superelastic member in an arm which connects an earpiece to a sound receiving transducer diaphragm, and that also provides a plurality of interchangeable transducer diaphragms which may be selected for use by a patient or user based on visible indicia on each of the diaphragms.

BACKGROUND

A stethoscope is an essential diagnostic instrument used in daily medical practice. In the clinical setting, the stethoscope is used as a listening device to evaluate heart, respiratory, pleural, uterine, intestinal and other physiological sounds which may be conveyed to the user. In fact, the wide spread use of stethoscopes is so thoroughly associated with medical care that the depiction of a dangling stethoscope hanging one's neck has become a caricature for physicians and other healthcare providers worldwide. However, perhaps in part due to this prevalent use of stethoscopes, these instruments of basic necessity have also become the object of much development and innovation.

Stethoscopes generally include a sound receiving portion, which often is a transducer diaphragm (usually a membrane-like partitioning surface), which is acoustically connected to two earpieces. The sound usually monitored by the diaphragm is generally a surface sound which is transmitted from various locations on the body surface through the diaphragm when pressed firmly on the body surface. Common stethoscope designs acoustically connect the diaphragm with the earpieces with an arm which bifurcates into a headset or earpiece assembly and which also carries a sound transmission member, such as a lumen channel or passageway, for the acoustic passage of the monitored surface sound. Moreover, most known stethoscopes further operate by filtering extraneous noise and modifying the incoming sound as it is transmitted to the earpieces.

Some known stethoscopes use stethoscope covers which are designed to be temporarily secured onto the sound receiving portion of the stethoscope for the intended purpose of addressing concerns at the diaphragm-patient interface when the diaphragm is pressed against the body surface. For example, one previous disclosure describes placing a cover on a stethoscope's sound receiving portion for the intended purpose of preventing the passage of contaminants and transmission of disease as the same stethoscope is used among various patients. Such covers are typically slid over the existing diaphragm piece, and may be composed of a thin coating, such as for example a latex membrane. Other covers have also been applied to a diaphragm surface of a stethoscope for an intended "insulatory" purpose. In this instance, the cover is intended to control the temperature of the instrument surface, such as by heating or thermal insulation, prior to physical contact with the mammalian body surface.

Other known stethoscopes have also used covers for the intended purpose of protecting the user-physician or other healthcare provider from skin irritations arising from instrument contact. For example, one previous disclosure describes use of a decorative hypoallergenic fabric stethoscope machine-washable cover which envelops the central portion or arm of the stethoscope. The fabric cover is applied by hook-and-loop or snap fasteners. Furthermore, there exists a decorative stethoscope sleeve which covers the portion of the stethoscope in contact with the neck of the user, applied to the instrument by the use of drawstrings.

Specific examples of stethoscope covers according to the various "protective" and "insulating" categories just summarized above are disclosed variously throughout the following references: U.S. Pat. No. 5,539,162 to Tuttle; U.S. Pat. No. 5,592,946 to Eddy; U.S. Pat. No. 4,867,265 to Wright; U.S. Pat. No. 4,871,046 to Turner; U.S. Pat. No. 5,269,314 to Kendall et al.; U.S. Pat. No. 5,428,193 to Mandiberg; U.S. Pat. No. 3,213,960 to Wagner. The disclosures of these references are herein incorporated by their entirety by reference thereto.

Conventional stethoscopes are further associated with other common, practical problems such as, for example: (1) undesirable and potentially harmful motion of the stethoscope as its flexible structure hangs from and swings about the neck of a healthcare provider; and (2) patient apprehension of the instrument before and during its application to the patient's body parts.

The undesired, swinging motion which may result from general use of conventional stethoscopes generally arises from the method of wearing the device when not in use. The common method for wearing a stethoscope includes placing the earpiece assembly around the neck as a virtual anchor which allows the arm and transducer assembly to hang vertically down the wearer's chest. However, the transducer is generally a heavy metallic implement and the arm is relatively flexible. This combination results in a wide pendulum-like member which may swing about a substantial arc during even the most subtle movements such as bending or reaching. Such a swinging motion of a heavy metallic transducer assembly may inconvenience either the user or the patient during a medical procedure, and may even result in harm to the user, the patient, the stethoscope itself, or other sensitive articles within reach of the stethoscope's swinging motion.

In attempt to prevent the potential harms and inconveniences just described in relation to the awkward nature of conventional stethoscope designs during normal use, many health care professionals will wrap the tubing of the stethoscope arm around their necks when not using the instrument. Even still, however, with most stethoscope designs these arm tubings are made of materials, such as for example latex, which may induce a hypoallergenic reaction when it comes into contact with the skin. It is believed that these potential dangers and inconveniences of the conventional stethoscope designs may be at least in part remedied by providing a stethoscope with a sound transmission arm that is designed to minimize or prevent swinging of the transducer assembly as the device is worn about a user's neck in a normal fashion.

Moreover, health professionals often find that some patients, especially the pediatric population, are apprehensive in the clinical setting and particularly to the application of medical devices such as stethoscopes to their body parts. To abate this uneasiness, there is a need to create a comfortable setting for such patients by making medical diagnostic instruments such as a stethoscope less intimidating. It is believed that providing appealing indicia, such as illustrations or graphical designs, on a stethoscope's transducer diaphragm outer surface may serve to at least partially pacify such an apprehensive patient prior to applying that surface to the patient's body. It is also believed that some patients may be further relieved of apprehension by providing a variety of such indicia or designs on interchangeable transducer diaphragms so that a particular indicia may be chosen for or by a given patient.

None of the cited references discloses a stethoscope device assembly that includes a sound transmission member with a super-elastic member which extends between an earpiece assembly and the sound receiver assembly such as a transducer diaphragm.

Nor do the cited references disclose a stethoscope device assembly that includes a releasably engaged transducer diaphragm member with indicia that is appealing to a patient such that the indicia is adapted to pacify the patient during a medical examination.

Nor do the cited references disclose a stethoscope device assembly which provides a plurality of such transducer diaphragms, each having a different appealing indicia, so that a patient or user of the stethoscope may chose a diaphragm based on a desired indicia.

SUMMARY OF THE INVENTION

The present invention is a stethoscope device assembly which is adapted to monitor a surface sound on a body surface of a mammalian body. This stethoscope device assembly includes an earpiece assembly with at least one earpiece which is acoustically coupled to a sound receiver assembly. The sound receiver assembly includes a receiver surface, which is adapted to couple to the body surface, and also a sound receiver which is adapted to receive the surface sound. A sound transmission member is coupled to and extends between the earpiece and the sound receiver. An arm is also provided and is coupled to and extends between the earpiece assembly and the sound receiver assembly.

In one mode of the invention, the arm further includes a superelastic member. The superelastic member has a resting shape which is adjustable under an applied force to a strained shape. The superelastic member also has an elastic memory to the resting shape after being adjusted to the strained shape.

In one aspect of this mode, the superelastic member includes a superelastic metal alloy, which in still a further aspect may be an alloy of nickel and titanium.

In another aspect of this mode, the resting shape of the superelastic member is adapted to minimize the arc about which the sound receiver assembly may swing when the stethoscope is worn by a user such that the earpiece assembly is engaged to the user's head or neck and the arm extends vertically downward therefrom along the user's chest. In a further variation of this aspect, the resting shape includes at least in part a helix.

In another mode of the invention, the sound receiver of the sound receiver assembly includes a housing and a transducer diaphragm which is adapted to removably engage the housing. When removably engaged with the housing, the transducer diaphragm is also adapted to couple to the body surface, in order to thereby receive the surface sound, and further includes an outer surface with an indicia which is adapted to be seen by the patient prior to monitoring the surface sound. According to this mode, the indicia imprinted upon the diaphragm is adapted to pacify an apprehensive patient. As the physician or other healthcare provider/user approaches the body surface of the patient with the diaphragm, the indicia is adapted to provide a visual distraction from the invasiveness of the physical examination, thus allowing the practitioner to carry out the diagnostic process with greater ease.

In one further aspect of this mode, the indicia includes an illustration which is adapted to pacify a pediatric patient which is apprehensive of contact with the transducer diaphragm.

In another aspect of this mode, a combination stethoscope device assembly includes both of: (1) an arm between the earpieces and the sound receiver assembly which also has a superelastic member with an elastic memory to a resting shape; and (2) a transducer diaphragm which is removably engageable with the sound receiver assembly and which includes an appealing indicia that is adapted to be seen by and pacify a patient.

In still another aspect of this mode, the stethoscope device assembly includes a plurality of transducer diaphragms. According to this aspect, each transducer diaphragm is adapted to removably engage the housing of the sound receiver assembly and has a different indicia than the other transducer diaphragms.

In yet a further aspect of this mode, the transducer diaphragm is adapted to couple to the body surface by directly contacting the body surface. In an alternative aspect, the transducer diaphragm is adapted to couple to the body surface indirectly. According to the latter alternative aspect, a protective cover is engaged to the housing and is coupled to the transducer diaphragm to create a sound transmissive barrier between the outer surface of the transducer diaphragm and the body surface.

Another mode of the present invention is a method for monitoring a surface sound on a body surface of a mammalian body with the stethoscope device assembly. The invention according to this mode includes selecting a transducer diaphragm from a plurality of transducer diaphragms based upon one particular indicia which is located on a surface of the transducer diaphragm and which is unique relative to other particular indicia located on the other transducer diaphragms. The transducer diaphragm is then releasably engaged to the sound receiver assembly, after which the transducer diaphragm is then coupled to the body surface. The surface sound is then received with the transducer diaphragm and is transmitted to the earpiece which is coupled to an ear of a user. Further to this method, the user may then listen to the surface sound.

In one aspect of this mode, the transducer diaphragm is chosen by the user of the stethoscope based upon a preferred one of the indicia.

In another aspect of this mode, the transducer diaphragm is chosen by the patient based upon a preferred one of the indicia.

Other features, advantages, and objects of the present invention will become apparent with reference to the following detailed description and accompanying drawings.

BRIEF DESCRIPTION OF THE DRAWINGS

FIG. 3 shows a longitudinal cross-sectional view of a similar sound receiver assembly as that shown in exploded view in FIG. 1.

FIG. 4 shows a perspective view of a plurality of transducer diaphragms, showing each transducer diaphragm with a different indicia such as: scenery, a graphic illustration, an item of sporting good equipment, and an illustration of a person, respectively.

DETAILED DESCRIPTION OF THE EMBODIMENTS

Figure 1:
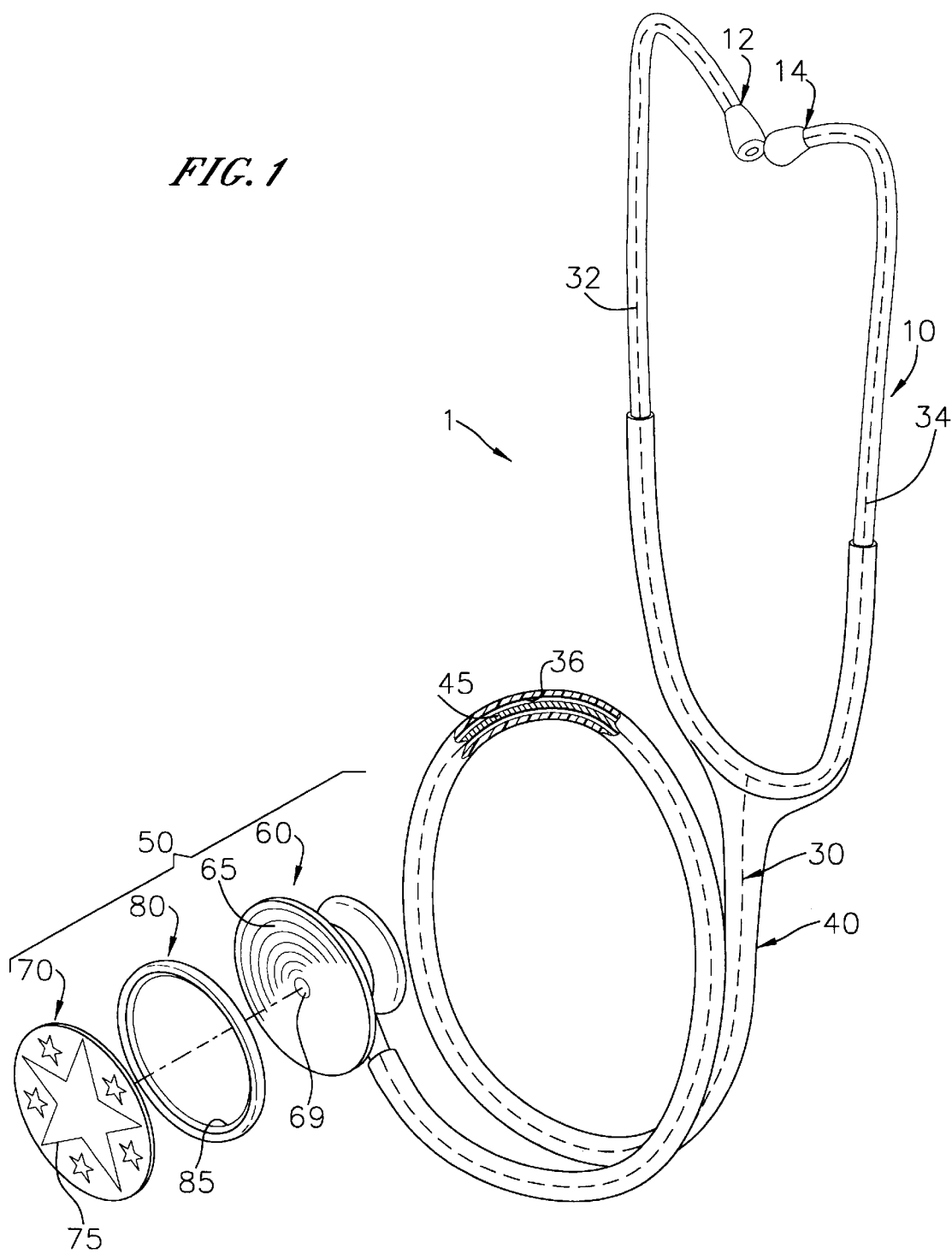
FIG. 1 shows a perspective view of a stethoscope device assembly according to the present invention, showing an earpiece assembly which is connected to a sound receiver assembly by an arm which includes a portion of a sound transmission member and which also includes superelastic member, and further showing the sound receiver assembly in an exploded perspective view.

FIG. 1 shows stethoscope device assembly (1) to include an earpiece assembly (10) which is acoustically coupled to sound receiver assembly (50) via sound transmission member (30) which is in-part contained within arm (40). More details regarding these particular elements of the present invention are provided as follows.

More particularly regarding earpiece assembly (10), FIG. 1 shows earpiece assembly (10) to include right and left earpieces (12,14) which are adapted to couple with right and left ears, respectively, of a user (not shown). According to the specific embodiment of FIG. 1, right and left earpieces (12,14) are connected to each other at or adjacent to arm (40) and bifurcate proximally therefrom. The arcuate shape shown in FIG. 1 for the earpieces provides combined overall shape which extends proximally with a diverging portion and a converging portion.

Right and left earpieces (12,14) are also shown in FIG. 1 to include right and left sound transmission members (32, 34) which, together with lower sound transmission member (36), form sound transmission member (30). Lower sound transmission member (36) is acoustically coupled to a sound receiver in the sound receiver assembly, which is described in more detail below. Surface sounds received by the sound receiver are transmitted proximally along lower sound transmission member (36) and right and left sound transmission members (32,34) to the right and left ears of the user. Lower sound transmission member (36) may comprise separate, isolated members which are virtual extensions of right and left sound transmission members (32,34), thereby allowing right and left earpieces (12,14) to communicate separately with sound receiver assembly (50). Or, lower sound transmission member (36) may comprise a single, common member from which right and left sound transmission members bifurcate at earpiece assembly (10). Lower sound transmission member (36) is shown in a cut-away view in FIG. 1 as a lumen passageway through which the surface sound is transmitted, thereby providing one particular embodiment for sound transmission member (30).

Figure 2A:
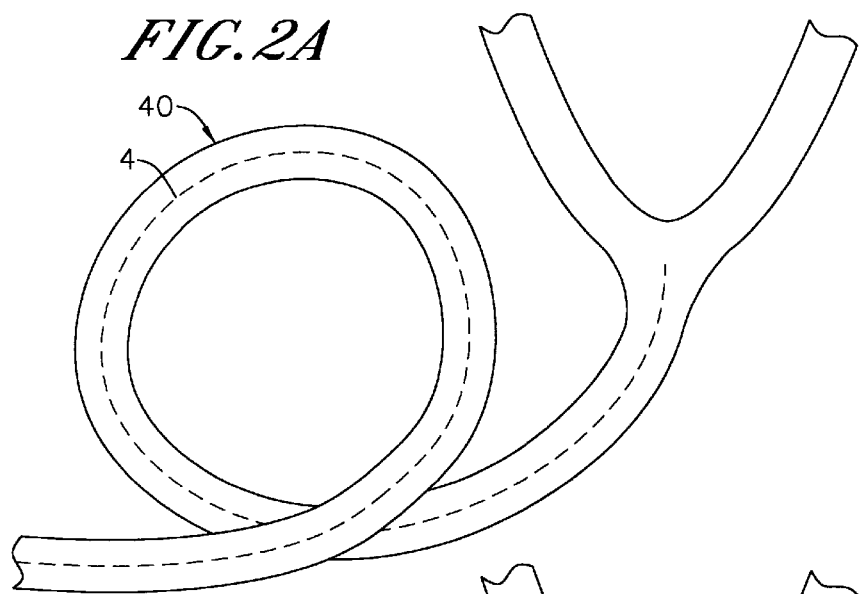
FIG. 2A shows a cut-away perspective view of a stethoscope device assembly similar to that shown in FIG. 1, showing an arm with a superelastic member, shown in shadowed view, in a resting shape which is a partial helix.
Figure 2B:
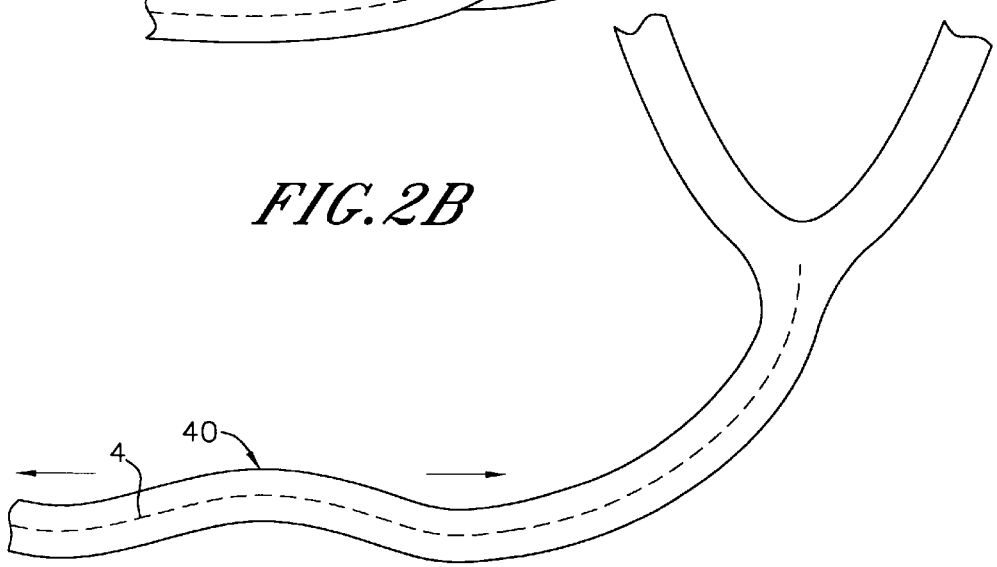
FIG. 2B shows a similar perspective view as that shown in FIG. 2A, although showing the arm after the superelastic member has been adjusted under an applied force from the resting shape to a strained shape.
Figure 2C:
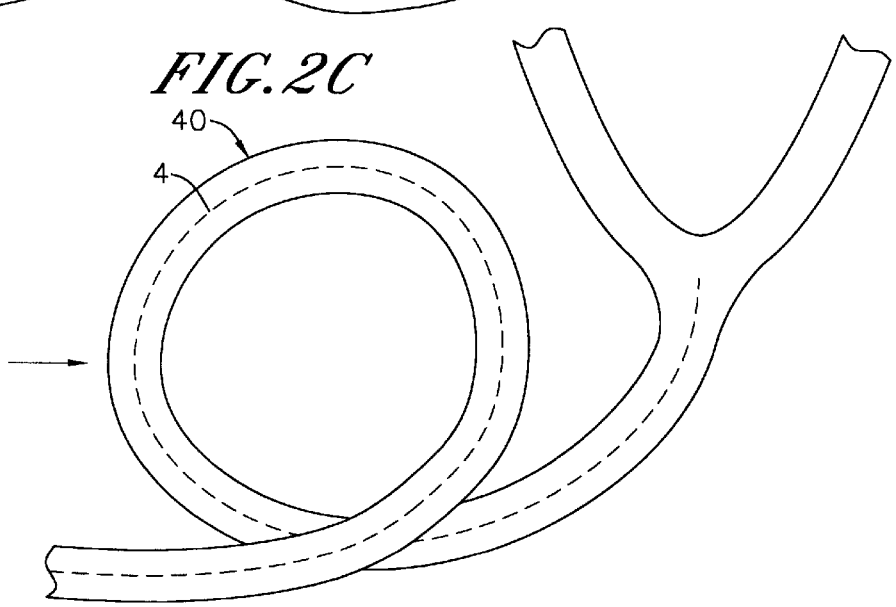
FIG. 2C shows another perspective view as that shown in FIGS. 2A–B, although illustratively showing with arrows the arm after the superelastic member has returned from the strained shape to the resting shape due to an elastic memory to the resting shape.

Arm (40) is also shown in FIG. 1 to include both lower sound transmission member (36) and a superelastic member (45). Superelastic member (45) is comprised at least in part of super-elastic materials, which may include for example an alloy of nickel and titanium, or more particularly Nitinol™ or Elastinite™ material. As is further shown in FIG. 1, and also by reference to FIG. 2A, arm (40) is shown to have a partial helical shape which is characterized by the resting condition or shape of the superelastic member (45). As is further illustrated in FIG. 2B, superelastic member (45) is adjustable under an applied force from the resting shape to a strained shape. Further to FIG. 2C, superelastic member (45) also has a memory to the resting shape when the applied straining force is removed.

Further to the specific superelastic member embodiment shown in FIG. 1, superelastic member (45) is shown as a mandrel type member which is disposed within the lumenal passageway which forms at least in part the sound transmission member (30), however, the present invention further contemplates that the superelastic member of the arm may be take other structural forms. For example, an alternative superelastic member may include a helical type structure or braid, which helix or braid itself the lumenal passageway of the sound transmission member. Furthermore, for the purpose of further illustration, such coiled or braided superelastic member may be embedded in a matrix or polymer to form a composite tubing that forms the lumenal passageway forming the sound transmission member.

The preshape and memory aspects of the superelastic member in the stethoscope's arm are provided in order to minimize or prevent the danger of unwanted swinging motion of the sound receiver assembly as the overall stethoscope assembly is worn around a user's neck. The resting helical shape shortens the effective length of the stethoscope's body or arm when not in use. The sound receiver assembly may be stretched from that resting shape to the strained shape to lengthen the arm in order to apply the sound receiver to the patient's body surface. Thereafter releasing the sound receiver allows the assembly to return to the resting shape until used again.

Returning to FIG. 1, and also by reference to FIG. 3, sound receiver assembly (50) is shown to include a transducer diaphragm (70) which is removably engageable to housing (60) by virtue of a retainer ring (80). In the particular embodiment shown, retainer ring (80) includes a groove (85) which is adapted to couple to both transducer diaphragm (70) and also to housing (60), thereby temporarily securing the two components together. A tapered surface (65) of the housing (60) forms a sound chamber defined in part when coupled with the transducer diaphragm (70) as shown in FIG. 3. As is further shown in FIG. 1, an aperture (69) which is formed by the tapered surface (65) of the housing (60) couples the sound receiver assembly to the sound transmission member (30).

The transducer diaphragm (70), when engaged to housing (60), is adapted to provide a receiver surface which may be pressed against and coupled to the body surface such that surface sounds may be received by the transducer. The present invention further contemplates use of an additional cover (not shown) which may be placed over the transducer diaphragm (70) according to the various intended uses of such stethoscope covers as summarized above. Moreover, other mechanisms for removably engaging transducer diaphragm with the housing of the sound receiver assembly of the present invention may be suitable, such as for example the use of discrete clips, brackets, or detents, as may be apparent to one of ordinary skill.

Transducer diaphragm (70) is further shown in FIG. 1 to include indicia, which is particularly shown as a graphical star-type pattern for the purpose of illustration. Other indicia may also be provided, such as scenery, sporting goods or balls, or a person's caricature or photo, as is shown for further illustration in FIG. 4. In addition, a kit which includes a plurality of such interchangeable transducer diaphragms which are each removably engageable with the housing of the sound receiver assembly may also be provided. Such a kit may include for example the plurality of transducer diaphragms (90) shown in FIG. 4, or may be a plurality of variations of each type of indicia shown (such as various types of scenarios, sports balls, designs or figures), or any other particular indicia as may be apparent to one of ordinary skill.

The removably engageable transducer diaphragm with indicia as just shown and described allows for a patient to identify with and be pacified by fears concomitant with an otherwise sterile and cold environment during the medical examination. Furthermore, the ability to chose from a kit of such interchangeably engagable transducer diaphragms allows a more significant involvement by the patient in the overall process. In fact, in one further variation of the present invention the indicia may further include a depiction, portrait, or actual photograph of the actual patient which may be stored by a regular physician or treatment facility. It is believed that the beneficial features just described by reference to the interchangeable indicia on the transducer of the invention may be particularly useful in the pediatric treatment environment where pictures or other illustrations which a patient identifies may help reduce apprehension to the diagnostic use of the scope on the patent's body surfaces. In addition, the indicia contemplated may also include advertisements in a more commercial application of the present invention, such as for example trademarks or logo's.

The present invention further contemplates use of sound receivers and/or receiver surfaces for the sound receiver assembly other than the specific transducer diaphragm embodiment just shown and described by reference to the Figures. For example, electronic chips or other transducers may be provided such that the receiver surface still bears the indicia according to the present invention. Also, where removable covers are used, the "receiver surface" may still be a transducer diaphragm such as previously described above, but is merely "coupled" to the body surface by means of the additional cover. Further to the indicia aspect of the invention according to this variation, the present invention contemplates that indicia on a receiver surface which is "perceived" by a patient to be coupled to the patient's body surface, even if through a thin membrane cover, is considered to fall within the present invention so long as the patient is provided the opportunity to view the indicia contemporaneous with or prior to use.

Several beneficial embodiments of the present invention have just been described in detail by reference to the Figures. However, other modifications or improvements from these particular embodiments may be made by one of ordinary skill based upon this disclosure without departing from the intended scope.

For example, the beneficial features just described may be taken individually or in combination according to the present invention. For example, the superelastic preshaped member in the arm and the removably engageable transducer diaphragm with indicia are each beneficial features which are considered both exclusively of each other and also in combination. In another example, particular structural features described which constitute components of an overall stethoscope device assembly are also contemplated as stand alone devices according to the present invention. For instance, the invention contemplates the transducer diaphragm described by reference to the embodiments in the Figures as a stand alone device which is adapted to removeably engage a stethoscope device assembly, in addition to the combination assembly which results. A similar example is provided by the arm which includes a superelastic member, which is considered in a combination stethoscope assembly, as well as a separately useful device which may be removeably engaged with a stethoscope device assembly.

In another example, transmission of a "surface sound" along the various components of an overall stethoscope assembly as described above may include modifications to the specific features or quality of that sound along the way. One such modification may include providing an amplifier along the overall sound transmitting assembly, such as for example in the sound receiver assembly, which transmits the sound from an initial or input condition (having an initial or input amplitude) at the body surface to an amplified condition or state (having a larger amplified amplitude) which is transmitted to the earpieces. Moreover, various filters may be used to similarly alter the quality of the surface sound whereas the filtered result should still be considered the "surface sound" according to the present invention.

Furthermore, other modifications such as providing one earpiece for one ear, rather than two earpieces for both ears, may be made without departing from the scope of the invention as provided in the claims which follow.

What is claimed is:

1. A stethoscope device assembly for monitoring a surface sound on a body surface of a patient during a medical diagnostic procedure, comprising:

an earpiece assembly with an earpiece which is adapted to couple to at least one of a right ear and a left ear of a user;

a sound receiver assembly with a housing and also with a transducer diaphragm which is removably engaged with the housing and which is adapted to couple to the body surface to thereby receive the surface sound, the transducer diaphragm further having an outer surface with an indicia which is visible when the transducer diaphragm is engaged with the housing; and a sound transmission member which is coupled the sound receiver assembly and also to the earpiece assembly and which is adapted to transmit the surface sound from the sound receiver and to the earpiece.

2. The stethoscope device assembly of claim 1, wherein the indicia further comprises an illustration which is adapted to pacify a pediatric patient.

3. The stethoscope device assembly of claim 1, further comprising:

an arm which comprises at least a portion of the sound transmission member and which further has a superelastic member with a resting shape, the superelastic member also being adjustable under an applied force to a strained shape and also having an elastic memory to the resting shape after being adjusted to the strained shape.

4. The stethoscope device assembly of claim 1, further comprising:

a plurality of transducer diaphragms, each transducer diaphragm being adapted to removably engage the housing of the sound receiver assembly and also having a different indicia than the other transducer diaphragms.

5. The stethoscope device assembly of claim 4, wherein the transducer diaphragm further comprises a circular member which is further comprised of a rigid polymer.

6. A transducer diaphragm for coupling to a housing of a sound receiver assembly in a stethoscope device assembly, comprising:

a diaphragm member with an inner surface and an outer surface and which is adapted to removeably engage the housing such that the outer surface may be coupled to a body surface, the diaphragm member being further adapted to receive a surface sound from the body surface when coupled to the body surface; and an indicia located on the outer surface which is adapted to pacify a patient.

7. A kit of transducer diaphragms for use in a stethoscope device assembly which includes a sound receiver assembly with a housing, comprising:

a plurality of diaphragm members, each diaphragm member having an inner surface and an outer surface and being adapted to removeably engage the housing such that the outer surface may be coupled to a body surface, each diaphragm member being further adapted to receive a surface sound from the body surface when coupled to the body surface; and a plurality of indicia, each being located on the outer surface of one of the diaphragm members and being further adapted to pacify a patient.

8. A method for monitoring a surface sound on a body surface of a mammalian body by using a stethoscope device assembly with a sound receiver assembly, an earpiece, and a sound transmission member which is coupled to the sound receiver assembly and also to the earpiece, comprising:

selecting a transducer diaphragm from a plurality of transducer diaphragms based upon one particular indicia which is located on a surface of the transducer diaphragm and which is unique relative to other particular indicia which is located on the other transducer diaphragms;

releasably coupling the transducer diaphragm to the sound receiver assembly;

coupling the transducer diaphragm to the body surface;

receiving the surface sound with the transducer diaphragm;

transmitting the surface sound from the transducer diaphragm and to the earpiece; and coupling the earpiece to an ear of a user;

listening to the surface sound by coupling the earpiece to an ear of the user when the transducer diaphragm is engaged with the sound receiver assembly and is coupled to the body surface.

9. The method of claim 8, wherein the transducer diaphragm is selected from the plurality of transducer diaphragms by the patient.

10. The method of claim 8, wherein the transducer diaphragm is selected from the plurality of transducer diaphragms by the user.

11. A stethoscope device assembly for monitoring a surface sound on a body surface of a patient during a medical diagnotistic procedure comprising:

an earpiece assembly with an earpiece which is adapted to couple to at least one of a right ear and a left ear of a user;

a sound receiver assumably with a housing and also with a transducer diaphragm which is removably engaged with the housing and which is adapted to couple to the body surface to thereby receive the surface sound, the transducer diaphragm further having an outer surface with an indicia which is visible when the transducer diaphragm is engaged with the housing:

a sound transmission member which is coupled the sound receiver assembly and also to the earpiece assembly and which is adapted to transmit the surface sound from the sound receiver and to the earpiece; and an arm which comprises at least a portion of the sound transmission member and which further has a superelastic member with a resting shape, the superelastic member also being adjustable under an applied force to a strained shape and also having an elastic memory to the resting shape after being adjusted to the strained shape.

12. A stethoscope device assembly for monitoring a surface sound on a body surface of a patient during a medical diagnostic procedure, comprising:

an earpiece assembly with an earpiece which is adapted to couple to at least one of a right ear and a left ear of a user;

a sound receiver assumable with a housing and also with a transducer diaphragm which is removably engaged with the housing and which is adapted to couple to the body surface to thereby receive the surface sound, the transducer diaphragm further having an outer surface with an indicia which is visible when the transducer diaphragm is engaged with the housing;

a sound transmission member which is coupled the sound receiver assembly and also to the earpiece assembly and which is adapted to transmit the surface sound from the sound receiver and to the earpiece; and a plurality of transducer diaphragms, each transducer diaphragm being adapted to removably engage the housing of the sound receiver assembly and also having a different indicia than the other transducer diaphragms.

13. The stethoscope device assebly of claim 12, wherein the transducer diaphragm further comprises a circular member which is further comprised of a rigid polymer.

\* \* \* \* \*